(12) United States Patent
Biddle et al.

(10) Patent No.: US 8,961,601 B2
(45) Date of Patent: Feb. 24, 2015

(54) IOL INJECTOR COMPRISING A MOVEABLE SIDE WALL

(75) Inventors: Graham W. Biddle, Ontario, NY (US); Jon P. Cullen, Churchville, NY (US); Emin Engin, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 1065 days.

(21) Appl. No.: 12/170,061

(22) Filed: Jul. 9, 2008

(65) Prior Publication Data

US 2010/0010498 A1 Jan. 14, 2010

(51) Int. Cl.
*A61F 9/00* (2006.01)
*A61F 2/16* (2006.01)

(52) U.S. Cl.
CPC .................................. *A61F 2/1664* (2013.01)
USPC ......................................... 623/6.12; 606/107

(58) Field of Classification Search
USPC .............. 604/59, 294; 606/107, 166; 623/4.1, 623/5.11, 5.14, 6.11–6.12, 6.18–6.21
See application file for complete search history.

(56) References Cited

U.S. PATENT DOCUMENTS

| 5,944,725 | A | 8/1999 | Cicenas et al. |
|---|---|---|---|
| 6,491,697 | B1 | 12/2002 | Clark et al. |
| 2005/0125000 | A1 | 6/2005 | Tourrette et al. |
| 2008/0294254 | A1 | 11/2008 | Cumming et al. |

*Primary Examiner* — Ashley Fishback
(74) *Attorney, Agent, or Firm* — Toan P. Vo

(57) ABSTRACT

An injector for inserting an intraocular lens (IOL) into an eye, comprising: a first side wall and a second side wall which are movable relative to one another, each side wall including a void, the voids positioned opposite one another in a direction perpendicular to a longitudinal axis of the injector. The injector may be in a combination with the IOL, the IOL disposed on a portion of the injector. The IOL may be in an unstressed state. A first portion of a haptic of the IOL may extend into the void in the first side wall.

18 Claims, 5 Drawing Sheets

IOL INJECTOR COMPRISING A MOVEABLE SIDE WALL

FIELD OF INVENTION

The present invention relates to an IOL injector and a method of using the same, and more particularly to an IOL injector comprising a moveable side wall and methods of using the same.

BACKGROUND OF THE INVENTION

A healthy human eye has an anterior chamber and a posterior chamber separated from one another by an iris. Within the posterior chamber is a capsular bag which holds the eye's natural crystalline lens.

Light enters the eye by passing through a cornea. The cornea and crystalline lens act together to direct and focus the light onto a retina. In response to the sharpness of the image received by the retina, the brain operates to contract or relax ciliary muscles.

In an eye where the natural crystalline lens has been damaged (e.g., clouded by cataracts), the natural lens is no longer able to properly focus and/or direct incoming light to the retina. As a result images become blurred. A well known surgical technique to remedy this situation involves removal of a damaged crystalline lens through a hole in the capsular bag known as a capsularhexis (also referred to simply as a rhexis). Subsequently, an artificial lens known as an intraocular lens (IOL) can be placed into the evacuated capsular bag through the rhexis.

Conventional IOLs are typically fixed-focus lenses. Such lenses are usually selected to have a power such that the patient has a fixed focus for distance vision, and the patient requires spectacles to permit near vision. In recent years extensive research has been carried out to develop IOLs having variable focus capability. Such IOLs are known as accommodating IOLs (AIOLS). AIOLs may be single-element or multi-element lenses.

AIOLs permit a wearer to have accommodative vision. AIOLs are typically located in the posterior chamber (e.g., in the capsular bag) and provide variable focal power in accordance with tension or a lack of tension exerted on the capsular bag as a result of contraction and relaxation of the ciliary muscle.

One example of a single-element AIOL is given in U.S. application Ser. No. 11/974,364, filed Oct. 11, 2007. The substance of said application is hereby incorporated by reference. A lens similar in relevant portions to the lens in FIG. 1A of said application is reproduced herein as FIG. 1. FIG. 1 illustrates an AIOL 100 comprising an optic 102 (also commonly referred to as an optical element), and two haptics 108a and 108b. The haptics comprise haptic plates 104a and 104b, respectively; and each haptic plate has two haptic filaments 106a and 106b, and 106c and 106d (also commonly referred to as loops).

Insertion of lenses which include a relatively complex haptic structure, such as lens 100, into an eye has proven complicated, particularly when insertion is performed using an IOL injector. For example, insertion using an injector (also referred to as injection) may result in haptic damage and/or incorrect orientation of the haptics.

SUMMARY

Aspects of the present invention are directed to methods and apparatus for injecting lenses having similar construction to the lens of FIG. 1. In particular, said methods and apparatus control bending of portions of the haptics and the optic to facilitate injection into an eye.

An aspect of the invention is directed to an injector for inserting an intraocular lens (IOL) into an eye, comprising a first side wall and a second side wall which are movable relative to one another, each side wall including a void, the voids positioned opposite one another in a direction perpendicular to a longitudinal axis of the injector.

In some embodiments, in an open position, said first side wall and said second side wall are positioned relative to one another to permit placement of the IOL therebetween, and in a closed position, said side walls are positioned relatively closer to one another than in the open position and define a passage for directing the IOL toward the eye. In some embodiments, the injector further comprises a tubular member having a lumen therethrough positioned relative to the passage such that, when walls are in the closed position, the lumen can receive a compressed IOL from the passage.

In some embodiments, the first side wall is fixedly attached to the tubular member and the second side wall is moveable relative to the tubular member. In some embodiments, the second side wall is moveable transverse to the longitudinal axis. The second side wall may be moveable perpendicular to the longitudinal axis.

In some embodiments, the injector is in a combination with the IOL, the IOL disposed on a portion of the injector. The IOL may be in an unstressed state when it is so disposed. In some embodiments, the IOL comprises a haptic, wherein a first portion of the haptic extends into the void in the first side wall. In some embodiments, a second portion of the haptic also extends into the void in the second wall.

In some embodiments, the void in the second side wall constitutes a gap formed between a first portion of the second side wall and a second portion of the second side wall. The void in the first side wall and the void in the second wall may each have a length in a direction parallel to the longitudinal axis of at least 0.5 mm.

Another aspect of the invention is directed to a method of compressing an IOL in an injector, the injector including a first side wall having a first void and a second side wall having a second void, the method comprising compressing the IOL by relatively moving the first side wall and the second side wall while a first haptic portion extends into the first void and a second haptic portion extends into the second void.

In some embodiments, during the step of compressing, the first portion and the second portion remain substantially uncompressed. In some embodiments, the step of compressing comprises moving the second side wall transverse to the longitudinal axis of the injector. The step of compressing may comprise moving the second side wall perpendicular to the longitudinal axis of the injector.

In some embodiments, the method further comprises locating the IOL on the injector in an unstressed state prior to the step of compressing. The step of locating the IOL in an unstressed state may comprise locating the IOL with the first haptic portion extending into the first void. In some embodiments, the first haptic portion and the second haptic portion are portions of a same haptic.

The term "distal portion" as used herein refers to a portion of a component that is relatively closer to the tip through which a lens is delivered into an eye than a corresponding "proximal portion".

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Figure 1:
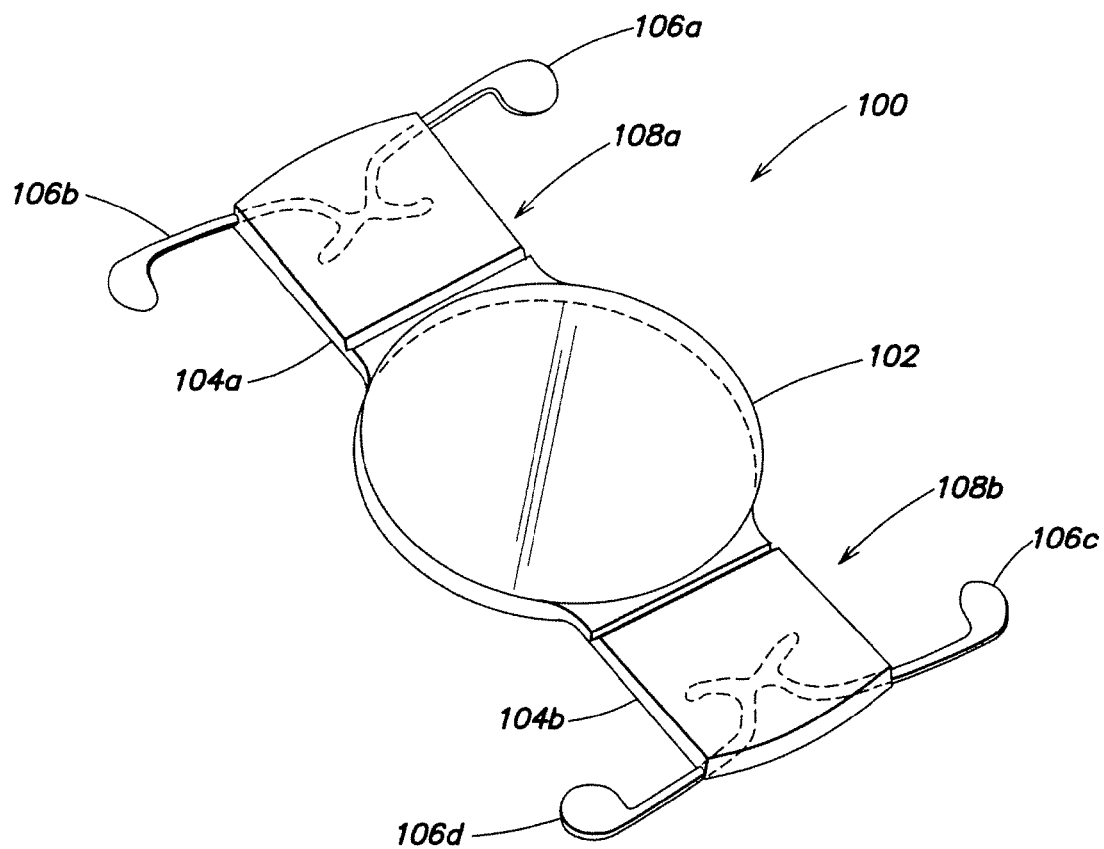
FIG. 1 is a schematic projection view of an example of an AIOL suitable for injection using techniques according to the present invention.
Figure 2:
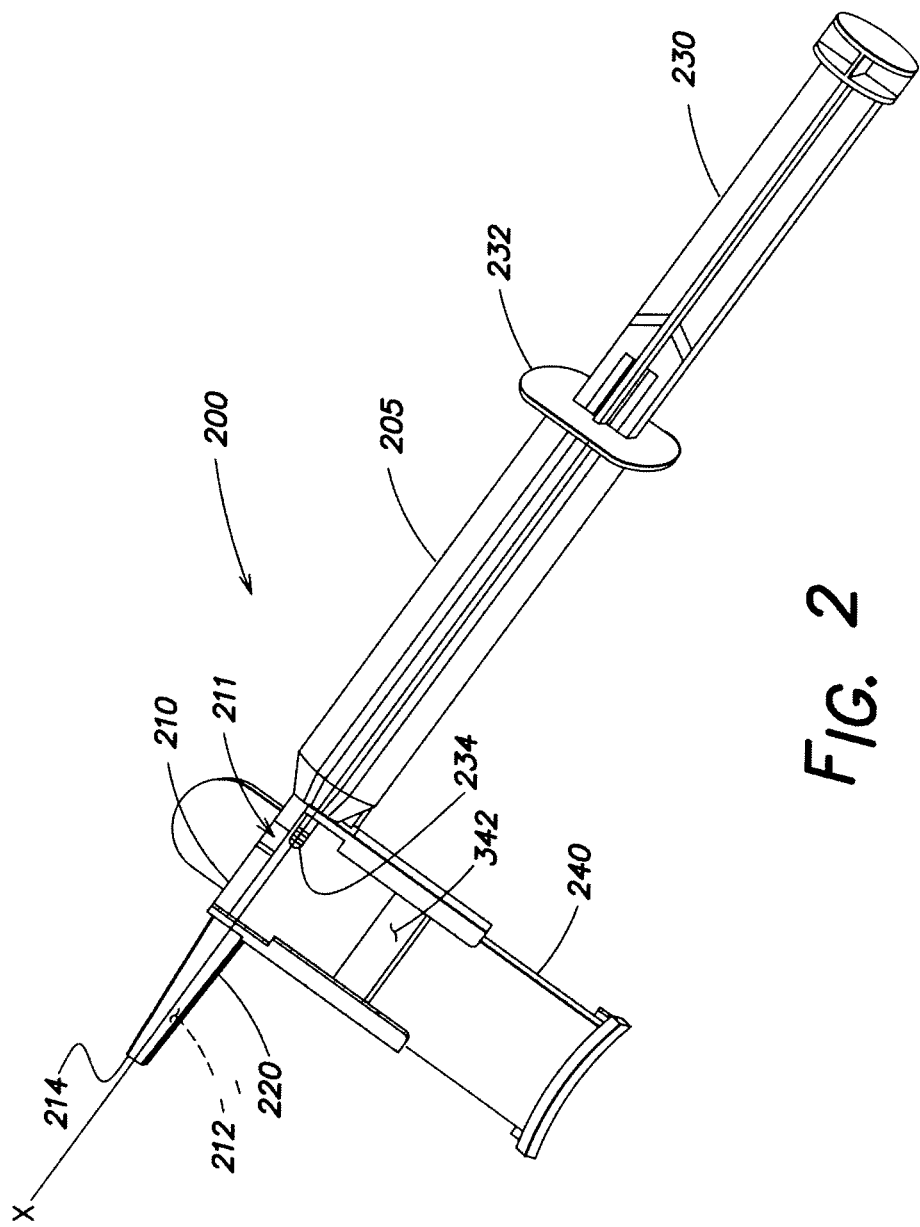
FIG. 2 is a schematic illustration of an example of an injector according to aspects of the present invention.

FIG. 2 is a schematic illustration of an example of an injector 200 according to aspects of the present invention. Injector 200 is suitable for inserting an intraocular lens (IOL) (e.g., the IOL described with reference to FIG. 1) into an eye. Injector 200 comprises an injector body 205, a first side wall 210, and a second side wall 310 (shown in FIG. 5) disposed on a compressor drawer 240. The first side wall and the second side wall are movable relative to one another between an open position (shown in FIG. 3) and a closed position. Injector 200 is shown in FIG. 4 in a partially closed position.

Figure 4:
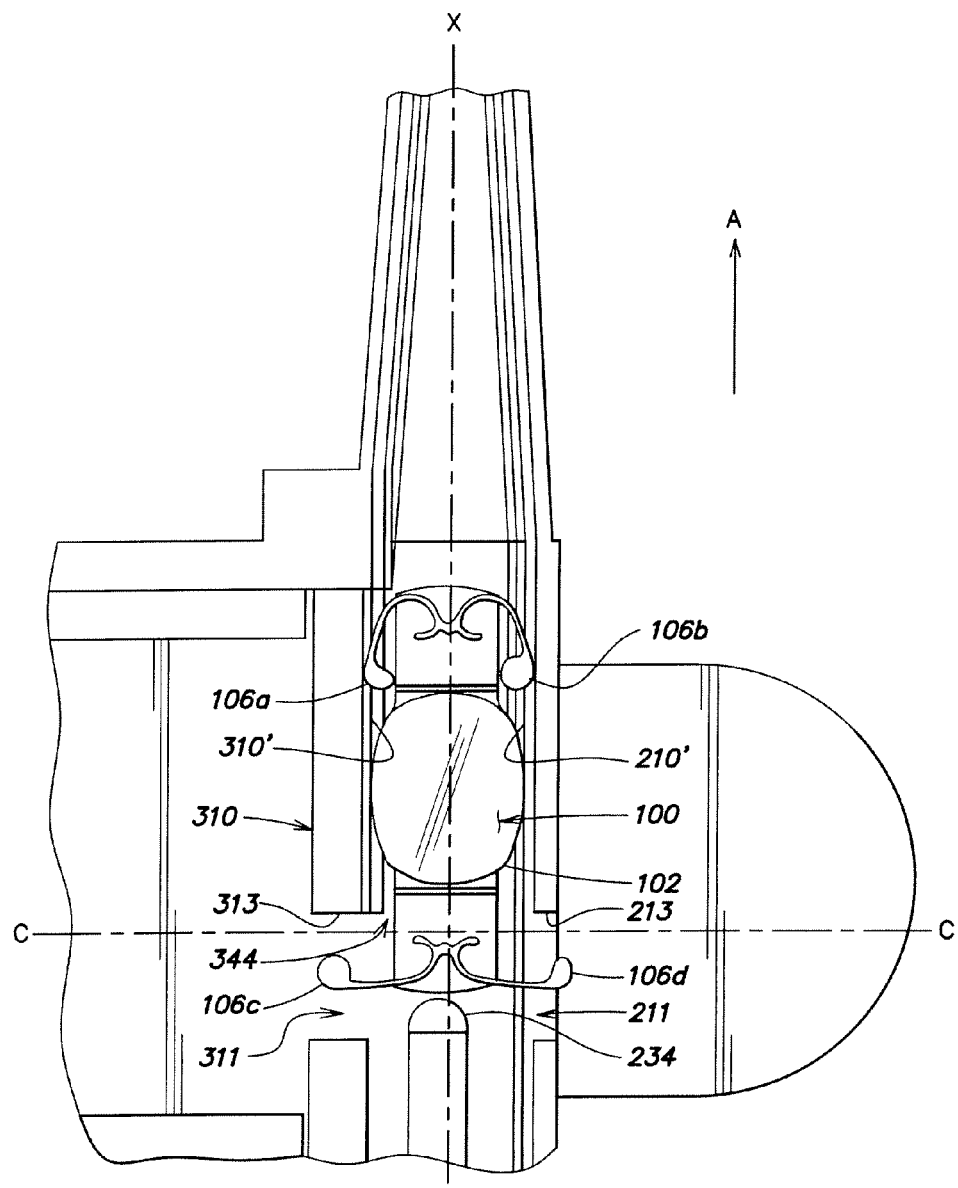
FIG. 4 is an expanded schematic illustration of the injector of FIG. 2 with an example of an IOL disposed thereon in a partially compressed state.

Referring again to FIG. 2, injector 200 also comprises a tubular member 220 having a lumen 212 therethrough coupled to said walls such that the lumen can receive a compressed IOL from a passage formed by surfaces of side walls 210 and 310 (as shown in FIG. 4). The tubular member includes a tip adapted to deliver a lens into an eye. Typically, the tip has an outer diameter that is relatively small to facilitate delivery of a lens through an incision in the eye that is less than 3.0 mm in diameter. Injector 200 also includes a plunger 230 for advancing a lens into an eye. Although a slidable plunger is illustrated, any suitable plunger may be used. For example, a screw-type plunger may be used. In some embodiments, the injector body comprises finger flange 232 to facilitate moving of the plunger. The tubular member may be integrally formed with the injector body or a separate component.

Figure 5:
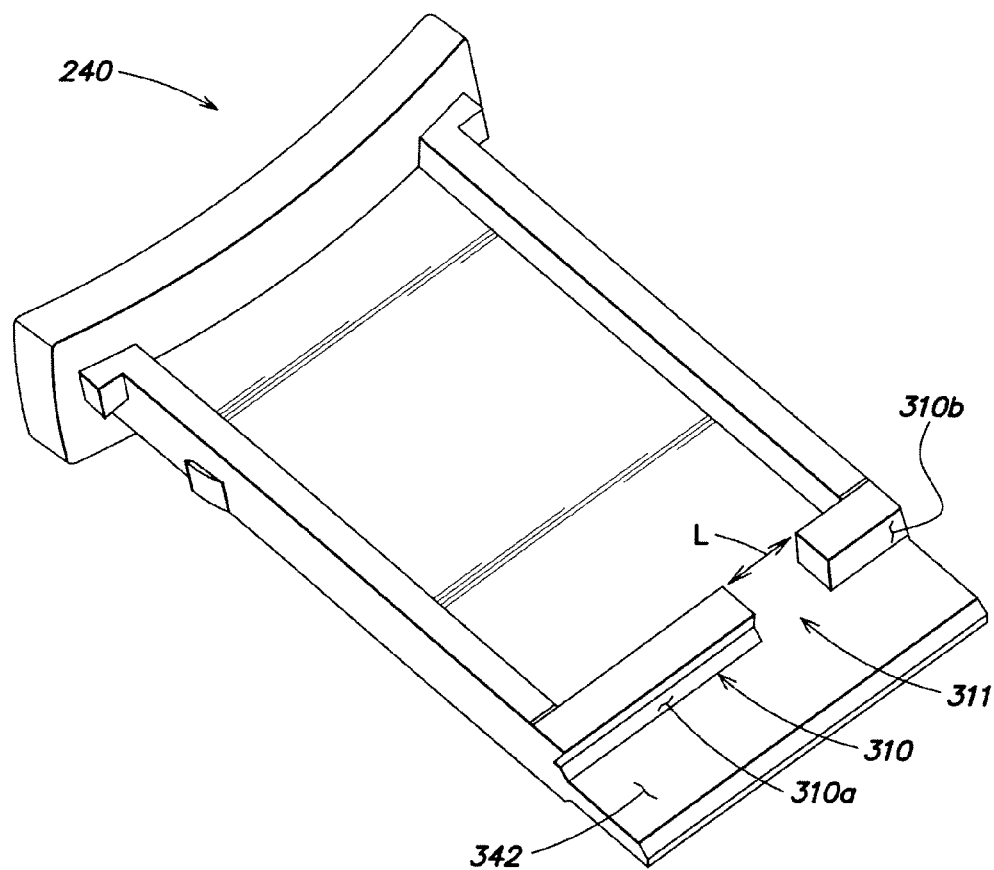
FIG. 5 is a projection view of a bottom of the compressor drawer of the injector of FIG. 2.

According to aspects of the present invention, each side wall 210, 310 includes a gap 211, 311. In the embodiment, first side wall 210 has a first gap 211. FIG. 5 is a bottom view of the compressor drawer 240 of the injector of FIG. 2. Second gap 311 is seen on the underside of compressor drawer as shown in FIG. 5. In the illustrated embodiment, an extension 342 extends beyond and over wall 310, so as to at least partially cover, and in some embodiments completely cover, an IOL as it is being compressed. In some embodiments extension 342, in combination with side walls 210 and 310 and loading deck 320, forms a complete passage (excluding the gaps) when the closed position is achieved.

In the illustrated embodiment, first side wall 210 constitutes a wall of an injector fixedly attached to the tubular member and injector body 205. The second side wall 310 constitutes a portion of the compressor drawer moveable relative to the tubular member and the injector body. The side walls are generally parallel to a longitudinal axis X of the injector. In some embodiments, the side walls may be slightly angled to compress the lens as it is advanced by the plunger.

Although in the illustrated embodiment only one wall 310 is moveable relative to the injector body, in other embodiment, both walls may be moveable. One or both side walls may be moveable transverse to longitudinal axis X. In some embodiments, the movement is perpendicular to longitudinal axis X. Also, although in the illustrated embodiment, wall 310 is slideable (e.g., translatable) relative to the injector body, other movement techniques may be implemented. For example, one or both walls may be pivotable or otherwise rotatable to achieve relative movement. Also, in the illustrated embodiment, the actuation mechanism of wall 310 includes a finger press for closing the compressor drawer; however any other suitable technique for actuation may be used including manual actuation or automated actuation.

Figure 3:
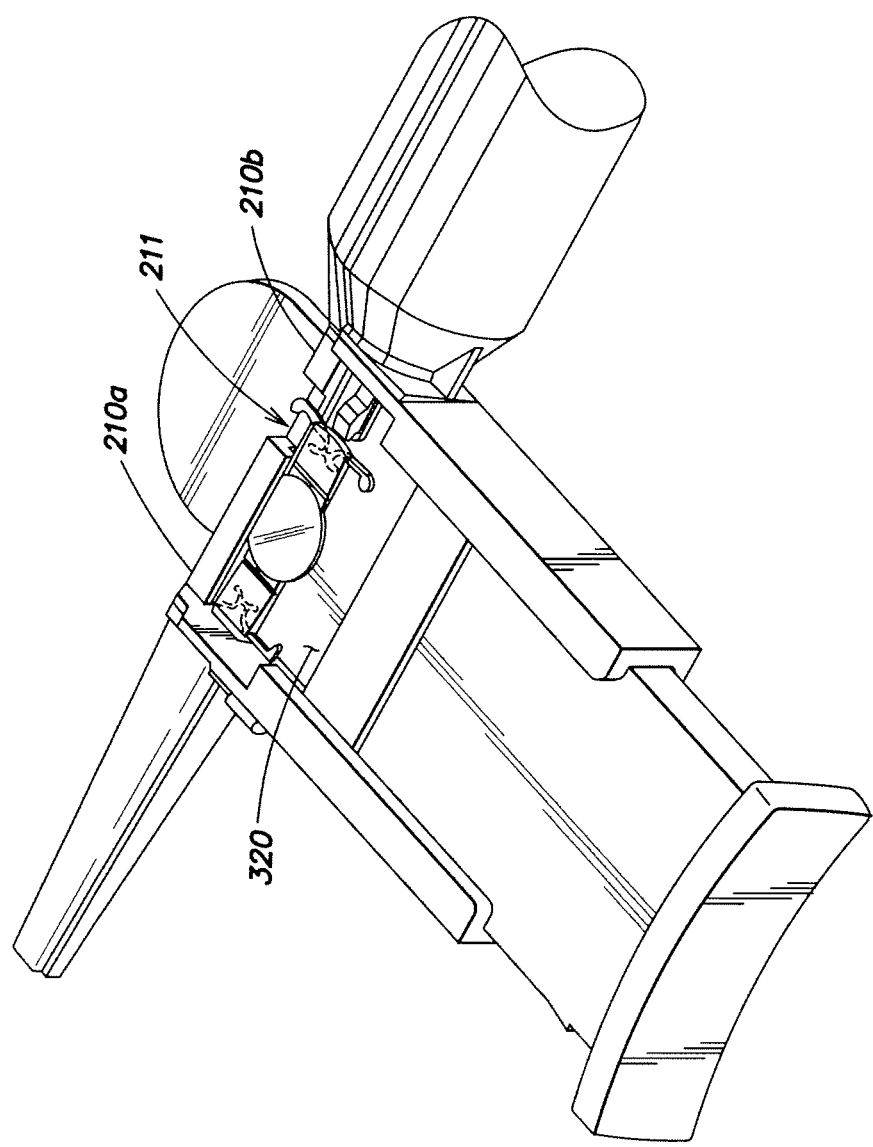
FIG. 3 is an expanded schematic illustration of the injector of FIG. 2 with an example of an IOL disposed thereon.

As shown in FIG. 3, in the open position, side wall 210 and side wall 310 (visible in FIG. 5) are positioned relative to one another to permit the placement of IOL 100 therebetween. That is, the walls can be separated to facilitate placement of the lens on loading deck 320. In some embodiments, the positioning of the walls permit placement of the IOL on the loading deck in an unstressed (i.e., unfolded) state as shown, with a face of the optic and/or faces of the haptics flat on the loading deck. However, in other embodiments a lens positioned on the loading deck may be at least partially folded.

In some embodiments, when the lens is placed on the injector, a portion of a haptic (e.g., a lens filament) extends into at least one of the gaps as shown in FIG. 3. However, in other embodiments, upon initial placement, no portions of a haptic may be positioned in a gap such that subsequent actuation is necessary to have a haptic portion extend into a gap; and in yet other embodiments, two or more portions of a haptic may extend into gap upon initial placement. In some embodiments, as would be understood from FIG. 3, the combination of the injector and an IOL is configured such that a first portion of a haptic of the IOL extends into the first gap upon placement of the lens on the loading deck and a second portion extends into the second gap only once the second wall is moved laterally (e.g., transverse to the longitudinal axis). It will be appreciated that, although the illustrated IOL embodiment has two portions of a single lens extending through the gaps, in some embodiments, the portions extending through the gaps may be portions of different haptics.

As shown in FIG. 4, in a partially closed position, side wall 210 and side wall 310 (visible in FIG. 5) are positioned relative to one another to laterally compress IOL 100 between the side walls and define a passage 344 for directing the flexible membrane toward an eye. In FIG. 4, extension 342 is omitted to facilitate viewing of the IOL and side walls 210 and 310. It will be appreciated that the side walls 210, 310 are closer to one another in the closed position than in the open position. Typically, in a fully closed position, the inner surfaces 210' and 310' of walls 210 and 310 will align with the corresponding surfaces of lumen 212 or the inner surfaces 210' and 310' will be located radially inward of the corresponding surfaces of the lumen to facilitate movement of a compressed IOL from the passage into the lumen without damage to the lens.

In FIG. 4, haptic filaments 106a, 106b and optic 102 are compressed; however, according to aspects of the present invention, the gaps 211, 311 are positioned opposite one another (in a direction perpendicular to longitudinal axis X of the injector) so as to permit compression of the lens without directly compressing a portion of the lens between gaps (e.g., filaments 106c, 106d).

The gaps at least partially align in direction perpendicular to longitudinal axis X, such that a line C-C, which is perpendicular to axis X, can extend through both gaps. In some embodiments, the gaps are symmetrically disposed about axis X.

Gaps may have any suitable length L to permit passage of the portions of the haptics (e.g., the filaments) into gaps such that compression of a lens can be achieved without direct compression of a lens portion (e.g., filaments 106c, 106d). It will be appreciated that compression "without direct compression of a portion of the lens" means that some folding of the non-directly compressed lens portion (e.g., filaments 106a, 106b) may occur due to compression of the remainder of the lens; however, the non-directly compressed portion will remain otherwise unfolded.

As used herein, the term "gap" refers to a configuration of a void that is located between wall portions, and the term "void" refers to any configuration where a portion of a wall is absent or has a reduced size. Although in the illustrated embodiment a gap formed between two wall portions is shown (e.g., gap 311 formed between portions 310a and 310b (see FIG. 5) or a gap 211 formed between portions 210a and 210b (see FIG. 3)), any suitable void configured to permit a portion of a haptic to fit therethrough may be used. It will be appreciated that a void may occur between two portions of a given wall (i.e., it forms a gap) or may be formed at an end of given wall, such that the void forms an opening disposed between a wall and another portion of the injector body. For example, a void at the end of the wall would occur if the side wall did not completely cover a moveable portion of the injector (e.g., compressor drawer 240) from side to side or if the side wall had reduced height at the side end of the moveable portion.

As illustrated, a void is sized and shaped to permit a portion of the lens (e.g., a portion of a haptic) to fit into and to remain substantially uncompressed when the injector is in a closed position. The voids permit the filaments 106c, 106d to freely fit therein. For example, in some embodiments, the length of the voids (e.g., gaps 211 and 311) in a direction parallel to the longitudinal axis is at least 0.5 mm, and in some embodiments said gap lengths are at least 0.75 mm. Also, in some embodiments, the depths of the gaps in a direction perpendicular to the longitudinal axis is at least 0.5 mm, and in some embodiments said gap depths are at least 0.75 mm. It will be appreciated that a width of a gap may be determined by a thickness of a corresponding wall. The term "substantially uncompressed" means unfolded except for possible folding due to non-direct compression.

It will be appreciated that lumen 212 of the tubular member 220 is coupled to said walls 210, 310 with lumen 212 positioned relative to the passage 344 such that, when walls are in the closed position, the lumen can receive a compressed IOL from the passage and can be directed into an a patient's eye. It will be appreciated that, when the walls are in a fully closed position optic 102 will be folded. It will also be appreciated that, after the walls are in a fully closed position, upon advancement of lens 100 by plunger tip 234 in the direction of arrow A, filaments 106c, 106d will be flexed in a reward direction (i.e., opposite of the direction of arrow A) thereby reducing the likelihood of damage to the said filaments. Flexing of the filaments will occur, for example, due to interference with the ends 213, 313 of walls 210, 310 as the lens is advanced.

Further details of an injector comprising a compressor drawer are given in U.S. Pat. No. 5,944,725, to Ciencas et al, issued Aug. 31, 1999. The substance of said patent is hereby incorporated by reference. It will be appreciated that injector described in said patent does not include voids as described herein.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. An injector for inserting an intraocular lens (IOL) into an eye, the injector having a lumen, a distal tip and a longitudinal axis extending through the lumen, the injector comprising:
    a first side wall and a second side wall which are movable relative to one another, the first side wall including a first void in a direction parallel to the longitudinal axis, the first void dividing the first side wall perpendicular to the longitudinal axis into a first proximal portion and a first distal portion, the first distal portion being closer to the distal tip than the first proximal portion along the longitudinal axis, the second side wall including a second void in a direction parallel to the longitudinal axis, the second void dividing the second side wall perpendicular to the longitudinal axis into a second proximal portion and a second distal portion, the second distal portion being closer to the distal tip than the second proximal portion along the longitudinal axis, the first and the second voids positioned opposite one another in a direction perpendicular to the longitudinal axis of the injector and
    wherein a first width measured between the first side wall and the second side wall, the first width measured in the direction perpendicular to the longitudinal axis, is less than a second width measured in the direction perpendicular to the longitudinal axis where the voids are located.

2. The injector of claim 1, wherein, in an open position, said first side wall and said second side wall are positioned relative to one another to permit placement of the IOL therebetween, and in a closed position, said side walls are positioned relatively closer to one another than in the open position and define a passage for directing the IOL toward the eye.

3. The injector of claim 2, further comprising a tubular member having a lumen therethrough positioned relative to the passage such that, when walls are in the closed position, the lumen can receive a compressed IOL from the passage.

4. The injector of claim 3, wherein the first side wall is fixedly attached to the tubular member and the second side wall is moveable relative to the tubular member.

5. The injector of claim 1, wherein the second side wall is moveable transverse to the longitudinal axis.

6. The injector of claim 5, wherein the second side wall is moveable perpendicular to the longitudinal axis.

7. The injector of claim 1 in combination with an IOL, the IOL disposed on a portion of the injector.

8. The injector of claim 7, wherein the IOL is in an unstressed state.

9. The injector of claim 7, wherein the IOL comprises a haptic, wherein a first portion of the haptic extends into the first void.

10. The injector of claim 9, wherein a second portion of the haptic extends into the second void.

11. The injector of claim 1, wherein the first void and the second void each have a length in a direction parallel to the longitudinal axis of at least 0.5 mm.

12. The injector of claim 1, wherein at least one of the first void and the second void extends entirely through a corresponding one of the first side wall and the second side wall.

13. A method of compressing an IOL in an injector, the method comprising:

providing an injector, the injector having a lumen, a distal tip, and a longitudinal axis extending through the lumen, the injector comprising a first side wall and a second side wall which are movable relative to one another, the first side wall having a first void in a direction parallel to the longitudinal axis, the first void dividing the first side wall perpendicular to the longitudinal axis into a first proximal portion and a first distal portion, the first distal portion being closer to the distal tip than the first proximal portion along the longitudinal axis, the second side wall having a second void in a direction parallel to the longitudinal axis, the second void dividing the second side wall perpendicular to the longitudinal axis into a second proximal portion and a second distal portion, the second distal portion being closer to the distal tip than the first proximal portion, the first and second voids positioned opposite one another in a direction perpendicular to the longitudinal axis of the injector; and compressing the IOL by relatively moving the first side wall and the second side wall while a first haptic portion extends into the first void and a second haptic portion extends into the second void and, during the step of compressing, the first haptic portion and the second haptic portion remain substantially uncompressed.

14. The method of claim 13, wherein the step of compressing comprises moving the second side wall transverse to the longitudinal axis of the injector.

15. The method of claim 14, wherein the step of compressing comprises moving the second side wall perpendicular to the longitudinal axis of the injector.

16. The method of claim 13, further comprising locating the IOL on the injector in an unstressed state prior to the step of compressing.

17. The method of claim 16, wherein the step of locating the IOL in an unstressed state comprises locating the IOL with the first haptic portion extending into the first void.

18. The method of claim 13, wherein the first haptic portion and the second haptic portion are portions of a same haptic.

* * * * *